United States Patent
Patel

(10) Patent No.: US 9,926,278 B2
(45) Date of Patent: Mar. 27, 2018

(54) SULFONYL HYDRAZIDE COMPOUNDS AND A REGIO-SELECTIVE PROCESS TO PREPARE 4-AROYL PYRAZOLE DERIVATIVES

(71) Applicant: E. I. DU PONT DE NEMOURS AND COMPANY, Wilmington, DE (US)

(72) Inventor: Kanu Maganbhai Patel, Sugarland, TX (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 15/305,407

(22) PCT Filed: Apr. 14, 2015

(86) PCT No.: PCT/US2015/025737
§ 371 (c)(1),
(2) Date: Oct. 20, 2016

(87) PCT Pub. No.: WO2015/179038
PCT Pub. Date: Nov. 26, 2015

(65) Prior Publication Data
US 2017/0044109 A1    Feb. 16, 2017

Related U.S. Application Data

(60) Provisional application No. 62/002,574, filed on May 23, 2014.

(51) Int. Cl.
*C07C 311/49*  (2006.01)
*C07D 211/02*  (2006.01)
(Continued)

(52) U.S. Cl.
CPC .......... *C07D 231/12* (2013.01); *C07C 303/36* (2013.01); *C07C 311/49* (2013.01);
(Continued)

(58) Field of Classification Search
CPC ........................... C07C 311/49; C07D 211/02
See application file for complete search history.

(56) References Cited

U.S. PATENT DOCUMENTS

| 5,939,559 A | 8/1999 | Morimoto et al. |
| 6,030,926 A | 2/2000 | Morimoto et al. |

FOREIGN PATENT DOCUMENTS

| DE | 101674 | 11/1973 |
| WO | 2015/167795 A1 | 11/2015 |
| WO | 2015/191377 A1 | 12/2015 |

OTHER PUBLICATIONS

Engelmann, abstract of CaPlus Accession No. 1974:14870, DN 80:14870, pub. 1973.*

(Continued)

*Primary Examiner* — Rebecca L Anderson
*Assistant Examiner* — Karen Cheng

(57) ABSTRACT

Disclosed are compounds of Formula I, including all stereoisomers, (N-oxides), and salts thereof, wherein A and R are as defined in the disclosure.

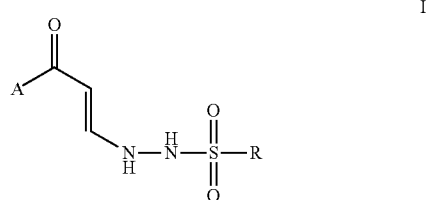

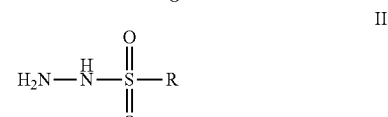

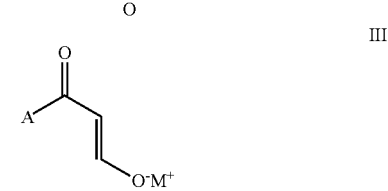

Also disclosed is a method for preparing a compound of Formula I, comprising reacting a compound of Formula II with an aroyl enolate salt of Formula III in the presence of an acid in an aqueous solvent mixture, wherein A, R and M are as defined in the disclosure.

Also disclosed is a method for preparing a compound of Formula IV, comprising reacting a compound of Formula I with an aldehyde of Formula V in the presence of a secondary amine salt, wherein A, B and R are as defined in the disclosure

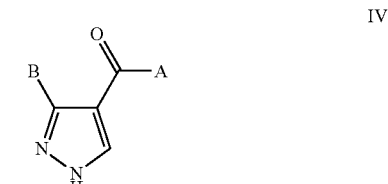

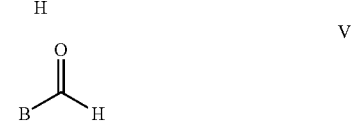

20 Claims, No Drawings

(51) Int. Cl.
  *C07D 231/12* (2006.01)
  *C07D 213/71* (2006.01)
  *C07D 231/16* (2006.01)
  *C07D 333/06* (2006.01)
  *C07D 333/28* (2006.01)
  *C07D 333/34* (2006.01)
  *C07D 239/26* (2006.01)
  *C07D 239/38* (2006.01)
  *C07D 261/08* (2006.01)
  *C07D 261/10* (2006.01)
  *C07D 277/28* (2006.01)
  *C07D 277/32* (2006.01)
  *C07D 277/36* (2006.01)
  *C07D 213/61* (2006.01)
  *C07D 307/52* (2006.01)
  *C07D 307/64* (2006.01)
  *C07C 303/36* (2006.01)

(52) U.S. Cl.
  CPC ......... *C07D 213/61* (2013.01); *C07D 213/71* (2013.01); *C07D 231/16* (2013.01); *C07D 239/26* (2013.01); *C07D 239/38* (2013.01); *C07D 261/08* (2013.01); *C07D 261/10* (2013.01); *C07D 277/28* (2013.01); *C07D 277/32* (2013.01); *C07D 277/36* (2013.01); *C07D 307/52* (2013.01); *C07D 307/64* (2013.01); *C07D 333/06* (2013.01); *C07D 333/28* (2013.01); *C07D 333/34* (2013.01)

(56) References Cited

OTHER PUBLICATIONS

STN RN 50591-82-7, entered into STN Nov. 16, 1984.*
I. Strakova et al., "3-Aryl and 2,3-Diaryl-4-oxo-4,5,6,7-tetrahydroindazoles. 1. Reactions of Phenyl and Tosylhydrazones of Dimedone and Cyclohexame-1,3-Dione with Substituted Benzaldehydes", Chemistry of Heterocyclic Compounds, Nov. 1, 2005, pp. 1398-1404, vol. 41, No. 11, Kluwer Academic Publishers-Consultants Bureau, NE.
Andrew J. Peat et al., "3-Trifluoromethyl-4-nitro-5-arylpyrazoles are novel KATP channel agonists", Bioorganic & Medicinal Chemistry Letters, Feb. 1, 2004, pp. 813-816, vol. 14, No. 3, Elsevier, Amsterdam, NL.
International Search Report for PCT/US2015/025737, dated Feb. 24, 2016.
Axel Angelmann Und Wolfgang Kirmse, Notiz zur Reaktion von 1-Phenyl-2-propin-1-on mit Hydrazinderivaten, Chem. Ber. (1973), 3092-3094, 106.

* cited by examiner

SULFONYL HYDRAZIDE COMPOUNDS AND A REGIO-SELECTIVE PROCESS TO PREPARE 4-AROYL PYRAZOLE DERIVATIVES

BACKGROUND OF THE INVENTION

A need exists for additional methods to prepare 4-aroyl pyrazole derivatives that are regio-selective and cost-effective. This invention relates to certain sulfonyl hydrazide compounds and the methods to prepare them. This invention also relates to a regio-selective, high yielding process to prepare 4-aroyl pyrazole derivatives that are useful as herbicides.

SUMMARY OF THE INVENTION

This invention is directed to a compound of Formula I (including all stereoisomers), N-oxides, and salts thereof

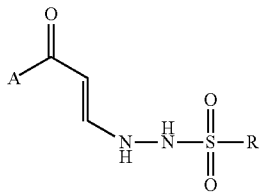

wherein
- A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy;
- R is $C_1$-$C_8$ alkyl optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy; or
- R is phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy.

This invention also relates to a method for preparing a compound of Formula I, comprising the step of reacting a compound of Formula II

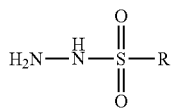

wherein
- R is $C_1$-$C_8$ alkyl optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy; or
- R is phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy;

with an aroyl enolate salt of Formula III

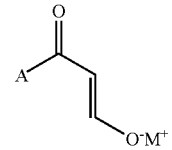

wherein
- M is an alkali metal or $NH_4$;
- A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy;

in the presence of an acid in an aqueous solvent mixture.

This invention also relates to a method for preparing a compound of Formula IV

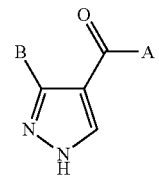

wherein
- A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy;
- B is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy;

comprising reacting a compound of Formula I

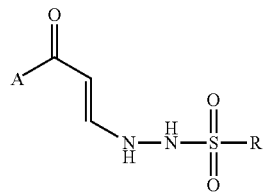

wherein
- R is $C_1$-$C_8$ alkyl optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy; or R is phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy;

with an aldehyde of Formula V

V in the presence of a secondary amine salt.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers. "Alkylamino", "dialkylamino", the like, are defined analogously to the above examples. "Cycloalkyl" includes, for example, cyclopropyl, cyclobutyl, cyclopentyl and cyclohexyl. The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkylthio" and the like, are defined analogously to the term "haloalkyl". Examples of "haloalkoxy" include $CF_3O$—, $CCl_3CH_2O$—, $HCF_2CH_2CH_2O$— and $CF_3CH_2O$—.

The total number of carbon atoms in a substituent group is indicated by the "$C_i$-$C_j$" prefix where i and j are numbers from 1 to 7. For example, $C_1$-$C_4$ alkyl designates methyl through butyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

Unless otherwise indicated, a "ring" or "ring system" as a component of Formula I is carbocyclic or heterocyclic. The term "ring system" denotes two or more fused rings. The term "ring member" refers to an atom or other moiety (e.g., C(=O), C(=S), S(O) or S(O)$_2$) forming the backbone of a ring or ring system.

The terms "heterocyclic ring" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. "weak or moderate acid" includes any acid that has pKa larger than −3 such as acetic acid, alkanoic acid, methane sulfonic acid, trifluoro acetic acid or poylphosphoric acid.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When A, B or R is a 5- or 6-membered heterocyclic ring, it may be attached to the remainder of Formula I though any available carbon or nitrogen ring atom, unless otherwise described. As noted above, A, B or R can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein $R^v$ is any substituents as defined in the Summary of the Invention for A, B or R and r is an integer (from 0 to 5). The number r is limited by the available carbon and nitrogen atom with free valency on the ring.

As noted above, A, B or R can be (among others) 5- or 6-membered heterocyclic ring, which may be saturated or unsaturated, optionally substituted with one or more substituents selected from a group of substituents as defined in the Summary of the Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention for A, B or R and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^V)_r$.

U-1
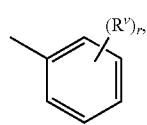

U-2
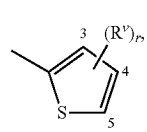

U-3
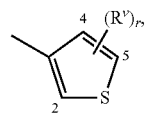

-continued

U-4
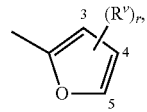

U-5
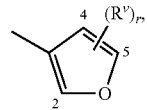

U-6
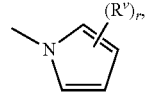

U-7
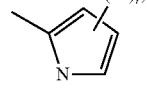

U-8
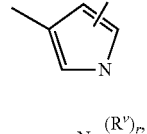

U-9
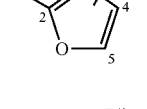

U-10
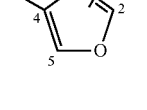

U-11
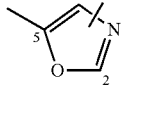

U-12
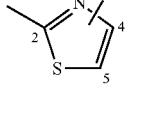

U-13
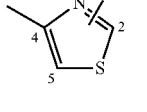

U-14
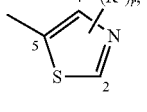

U-15
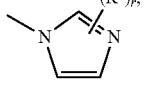

-continued
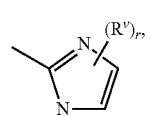 U-16
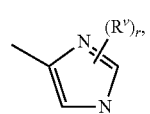 U-17
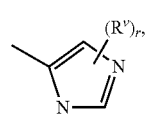 U-18
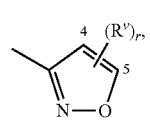 U-19
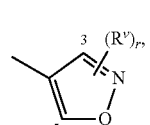 U-20
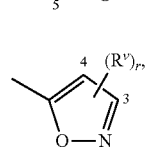 U-21
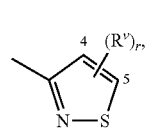 U-22
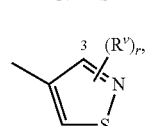 U-23
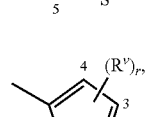 U-24
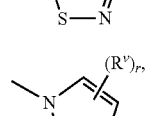 U-25
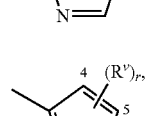 U-26
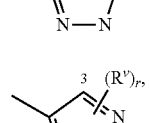 U-27
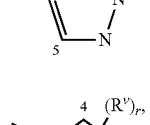 U-28
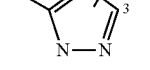
-continued
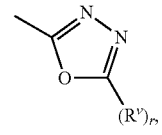 U-29
 U-30
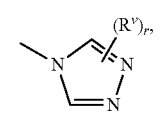 U-31
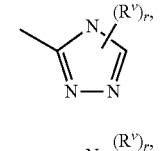 U-32
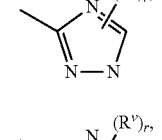 U-33
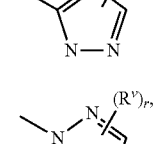 U-34
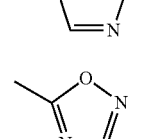 U-35
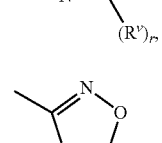 U-36
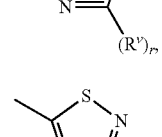 U-37
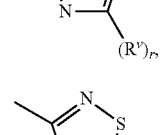 U-38
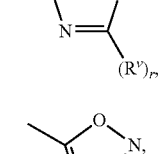 U-39
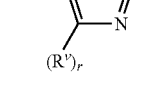 U-40

-continued

U-41 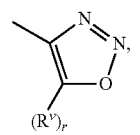

U-42 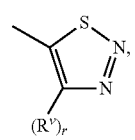

U-43 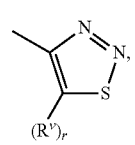

U-44 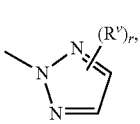

U-45 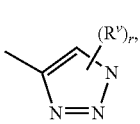

U-46 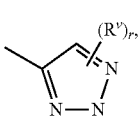

U-47 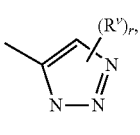

U-48 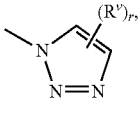

U-49 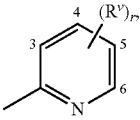

U-50 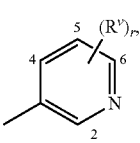

U-51 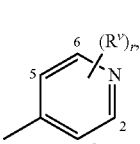

U-52 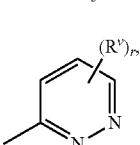

-continued

U-53 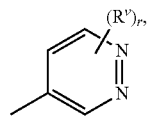

U-54 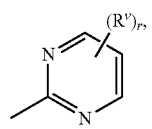

U-55 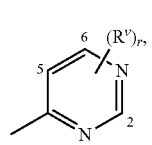

U-56 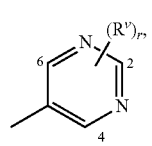

U-57 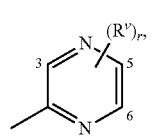

U-58 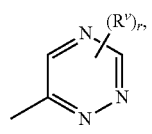

U-59 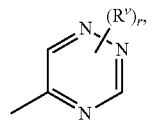

U-60 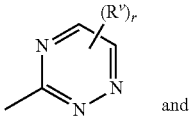

and

U-61 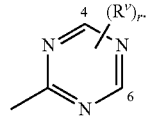

Note that when A, B or R is a 5- or 6-membered saturated or unsaturated non-aromatic heterocyclic ring optionally substituted with one or more substituents selected from the group of substituents as defined in the Summary of the Invention for A, B or R, one or two carbon ring members of the heterocycle can optionally be in the oxidized form of a carbonyl moiety.

Examples of a 5- or 6-membered saturated or non-aromatic unsaturated heterocyclic ring containing ring members selected from up to two O atoms and up to two S atoms, and optionally substituted on carbon atom ring members with up to five halogen atoms includes the rings G-1 through G-35 as illustrated in Exhibit 2. Note that when the attachment point on the G group is illustrated as floating, the G group can be attached to the remainder of Formula I through any available carbon or nitrogen of the G group by replacement of a hydrogen atom. The optional substituents corresponding to $R^v$ can be attached to any available carbon or nitrogen by replacing a hydrogen atom. For these G rings, r is typically an integer from 0 to 4, limited by the number of available positions on each G group.

Note that when A, B or R comprises a ring selected from G-28 through G-35, $G^2$ is selected from O, S or N. Note that when $G^2$ is N, the nitrogen atom can complete its valence by substitution with either H or any substituents as defined in the Summary of the Invention for A, B or R corresponding to $R^v$.

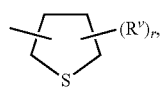
G-1

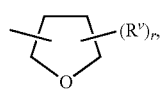
G-2

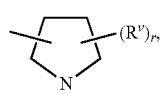
G-3

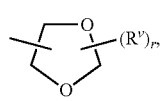
G-4

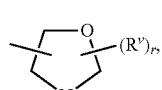
G-5

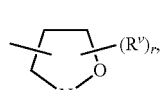
G-6

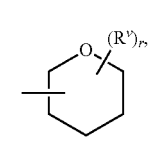
G-7

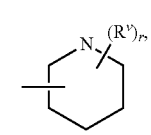
G-8

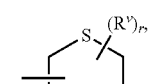
G-9

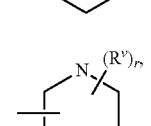
G-10

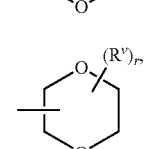
G-11

-continued

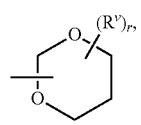
G-12

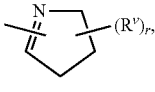
G-13

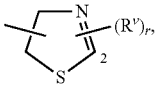
G-14

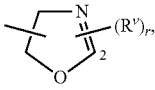
G-15

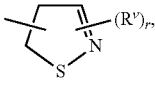
G-16

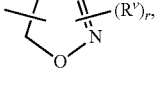
G-17

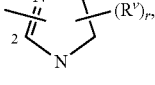
G-18

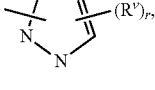
G-19

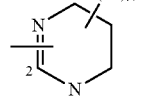
G-20

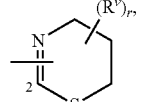
G-21

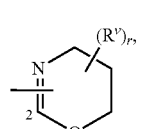
G-22

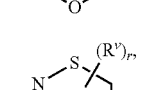
G-23

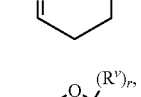
G-24

G-25

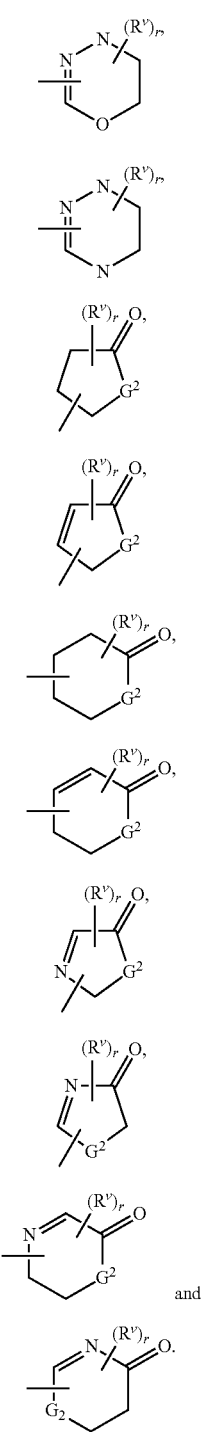

Although $R^v$ groups are shown in the structures U-1 through U-123, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of this invention can exist as one or more conformational isomers due to stereochemistry of the double bond in Formula I. This invention comprises mixtures of conformational isomers. In addition, this invention includes compounds that are enriched in one conformer relative to others.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. The salts of a compound of Formula I include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula I contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula I, N-oxides and salts thereof.

Embodiments of the present invention as described in the Summary of the Invention include (where Formula I as used in the following Embodiments includes N-oxides and salts thereof):

Embodiments of the present invention as described in the Summary of the Invention include the following:

Embodiment A1. A compound of Formula I as described in the Summary of Invention.

Embodiment A2. A compound of Embodiment A1 wherein A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment A3. A compound of Embodiment A2 wherein A is phenyl, naphthalenyl, or a 5- or 6-membered heterocyclic ring, each ring or ring system optionally substituted with halogen or $C_1$-$C_4$ alkyl.

Embodiment A4. A compound of Embodiment A3 wherein A is phenyl, naphthalenyl, or a 5- or 6-membered heterocyclic ring, each ring or ring system optionally substituted with halogen.

Embodiment A5. A compound of Embodiment A1 wherein A is phenyl, optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy.

Embodiment A6. A compound of Embodiment A5 wherein A is phenyl, optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment A7. A compound of Embodiment A6 wherein A is phenyl, optionally substituted with halogen or $C_1$-$C_4$ alkyl.

Embodiment A8. A compound of Embodiment A7 wherein A is phenyl, optionally substituted with halogen.

Embodiment A9. A compound of Embodiment A8 wherein A is phenyl substituted with halogen at 3- and 5-positions or 2- and 5-positions.

Embodiment A10. A compound of Embodiment A8 wherein A is phenyl, optionally substituted with up to 5 F.

Embodiment A11. A compound of Embodiment A1 wherein A is a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy.

Embodiment A12. A compound of Embodiment A11 wherein A is a 5- or 6-membered heterocyclic ring, each ring optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment A13. A compound of Embodiment A12 wherein A is a 5- or 6-membered heterocyclic ring, each ring optionally substituted with halogen or $C_1$-$C_4$ alkyl.

Embodiment A14. A compound of Embodiment A13 wherein A is a 5- or 6-membered heterocyclic ring, each ring optionally substituted with halogen.

Embodiment A14a. A compound of Embodiment A14 wherein A is 2-thienyl, 3-thienyl or 3-pyridyl, each optionally substituted with halogen.

Embodiment A15. A compound of Embodiment A1 wherein A is phenyl, 2-thienyl, 3-thienyl or 3-pyridyl, each optionally substituted with halogen or $C_1$-$C_4$ alkyl.

Embodiment A16. A compound of Embodiment A15 wherein A is phenyl or 2-thienyl, each optionally substituted with halogen or $C_1$-$C_4$ alkyl.

Embodiment A17. A compound of Embodiment A16 wherein A is phenyl or 2-thienyl, each optionally substituted with halogen.

Embodiment A18. A compound of Embodiment A17 wherein A is 2-thienyl, optionally substituted with halogen.

Embodiment A19. A compound of Formula I or any one of the Embodiments A1 through A18 wherein R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl or $C_1$-$C_4$ haloalkoxy.

Embodiment A20. A compound of Embodiment A19 wherein R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl or $C_1$-$C_4$ alkoxy.

Embodiment A20a. A compound of Embodiment A20 wherein R is $C_1$-$C_8$ alkyl.

Embodiment A21. A compound of Embodiment A20a wherein R is methyl.

Embodiment A22. A compound of Embodiment A20 wherein R is phenyl, optionally substituted with $C_1$-$C_4$ alkyl.

Embodiment A23. A compound of Embodiment A22 wherein R is 4-methylbenzene.

Embodiment B1. A method for preparing a compound of Formula I as described in the Summary of Invention.

Embodiment B2. A method of Embodiment B1 wherein A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment B3. A method of Embodiment B2 wherein A is phenyl, naphthalenyl, or a 5- or 6-membered heterocyclic ring, each ring or ring system optionally substituted with halogen or $C_1$-$C_4$ alkyl.

Embodiment B4. A method of Embodiment B3 wherein A is phenyl, naphthalenyl, or a 5- or 6-membered heterocyclic ring, each ring or ring system optionally substituted with halogen.

Embodiment B5. A method of Embodiment B1 wherein A is phenyl optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ di-alkylamino, cyano, nitro, $C_1$-$C_4$ alkoxy-carbonyl, phenyl or phenoxy.

Embodiment B6. A method of Embodiment B5 wherein A is phenyl optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment B7. A method of Embodiment B6 wherein A is phenyl optionally substituted with halogen or $C_1$-$C_4$ alkyl.

Embodiment B8. A method of Embodiment B7 wherein A is phenyl optionally substituted with halogen.

Embodiment B9. A method of Embodiment B8 wherein A is phenyl optionally substituted with up to 4 halogens.

Embodiment B10. A method of Embodiment B9 wherein A is phenyl substituted with halogen at the 3- and 5-positions or at the 2- and 5-positions.

Embodiment B10a. A method of Embodiment B10 wherein the halogen is F.

Embodiment B11. A method of Embodiment B1 wherein A is a 5- or 6-membered heterocyclic ring, each ring optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ di-alkylamino, cyano, nitro, $C_1$-$C_4$ alkoxy-carbonyl, phenyl or phenoxy.

Embodiment B12. A method of Embodiment B11 wherein A is a 5- or 6-membered heterocyclic ring, each ring optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment B13. A method of Embodiment B12 wherein A is a 5- or 6-membered heterocyclic ring, each ring optionally substituted with halogen or $C_1$-$C_4$ alkyl.

Embodiment B14. A method of Embodiment B13 wherein A is a 5- or 6-membered heterocyclic ring, each ring optionally substituted with halogen.

Embodiment B14a. A method of Embodiment B14 wherein A is 2-thienyl, 3-thienyl or 3-pyridyl, each optionally substituted with halogen.

Embodiment B15. A method of Embodiment B1 wherein A is phenyl, 2-thienyl, 3-thienyl or 3-pyridyl, each optionally substituted with halogen or $C_1$-$C_4$ alkyl.

Embodiment B16. A method of Embodiment B15 wherein A is phenyl or 2-thienyl, each optionally substituted with halogen or $C_1$-$C_4$ alkyl.

Embodiment B17. A method of Embodiment B16 wherein A is phenyl or 2-thienyl, each optionally substituted with halogen.

Embodiment B18. A method of Embodiment B17 wherein A is 2-thienyl optionally substituted with halogen.

Embodiment B19. A method of any one of the Embodiments B1 through B18 wherein R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl or $C_1$-$C_4$ haloalkoxy.

Embodiment B20. A method of Embodiment B19 wherein R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl or $C_1$-$C_4$ alkoxy.

Embodiment B20a. A method of Embodiment B19 wherein R is $C_1$-$C_8$ alkyl.

Embodiment B21. A method of Embodiment B20 wherein R is Me.

Embodiment B22. A method of Embodiment B20 wherein R is phenyl optionally substituted with $C_1$-$C_4$ alkyl.

Embodiment B23. A method of Embodiment B22 wherein R is 4-methylbenzene.

Embodiment B24. A method of any one of Embodiments B1 through B23 wherein M is an alkali metal or $NH_4$.

Embodiment B25. A method of Embodiment B24 wherein M is an alkali.

Embodiment B26. A method of Embodiment B25 wherein M is Na or K.

Embodiment B27. A method of any one of Embodiments B1 through B26 wherein the acid is a weak or moderate acid.

Embodiment B28. A method of Embodiment B27 wherein the acid is an alkanoic acid.

Embodiment B29. A method of Embodiment B28 wherein the acid is formic, acetic or propionic acid.

Embodiment B30. A method of Embodiment B29 wherein the acid is acetic acid.

Embodiment B31. A method of any one of Embodiments B1 through B30 wherein the aqueous solvent mixture comprises an organic solvent.

Embodiment B32. A method of Embodiment B31 wherein the aqueous solvent mixture comprises an alcoholic solvent.

Embodiment B33. A method of Embodiment B32 wherein the aqueous solvent mixture comprises ethanol.

Embodiment B34. A method of any one of Embodiments B1 through B33 wherein the reaction temperature is from about −10° C. to about 110° C.

Embodiment B35. A method of Embodiment B34 wherein the reaction temperature is from about 0° C. to about 75° C.

Embodiment B36. A method of Embodiment B35 wherein the reaction temperature is from about 10° C. to about 25° C.

Embodiment B37. A method of Embodiment B35 wherein the reaction temperature is from about 20° C. to about 30° C.

Embodiment C1. A method for preparing a compound of Formula IV as described in the Summary of Invention.

Embodiment C2. A method of Embodiment C1 wherein A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment C3. A method of Embodiment C2 wherein A is phenyl, naphthalenyl, or a 5- or 6-membered heterocyclic ring, each ring or ring system optionally substituted with halogen or $C_1$-$C_4$ alkyl.

Embodiment C4. A method of Embodiment C3 wherein A is phenyl, naphthalenyl, or a 5- or 6-membered heterocyclic ring, each ring or ring system optionally substituted with halogen.

Embodiment C5. A method of Embodiment C1 wherein A is phenyl optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ di-alkylamino, cyano, nitro, $C_1$-$C_4$ alkoxy-carbonyl, phenyl or phenoxy.

Embodiment C6. A method of Embodiment C5 wherein A is phenyl optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment C7. A method of Embodiment C6 wherein A is phenyl optionally substituted with halogen or $C_1$-$C_4$ alkyl.

Embodiment C8. A method of Embodiment C7 wherein A is phenyl optionally substituted with halogen.

Embodiment C9. A method of Embodiment C8 wherein A is phenyl optionally substituted with up to 4 halogens.

Embodiment C10. A method of Embodiment C9 wherein A is phenyl substituted with halogen at the 3- and 5-positions or at the 2- and 5-positions.

Embodiment C10a. A compound of Embodiment C10 wherein the halogen is F.

Embodiment C11. A method of Embodiment C1 wherein A is a 5- or 6-membered heterocyclic ring, each ring optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ di-alkylamino, cyano, nitro, $C_1$-$C_4$ alkoxy-carbonyl, phenyl or phenoxy.

Embodiment C12. A method of Embodiment C11 wherein A is a 5- or 6-membered heterocyclic ring, each ring optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment C13. A method of Embodiment C12 wherein A is a 5- or 6-membered heterocyclic ring, each ring optionally substituted with halogen or $C_1$-$C_4$ alkyl.

Embodiment C14. A method of Embodiment C13 wherein A is a 5- or 6-membered heterocyclic ring, each ring optionally substituted with halogen.

Embodiment C14a. A method of Embodiment C14 wherein A is 2-thienyl, 3-thienyl or 3-pyridyl, each ring optionally substituted with halogen.

Embodiment C15. A method of Embodiment C1 wherein A is phenyl, 2-thienyl, 3-thienyl or 3-pyridyl, each ring optionally substituted with halogen or $C_1$-$C_4$ alkyl.

Embodiment C16. A method of Embodiment C15 wherein A is phenyl or 2-thienyl, each optionally substituted with halogen or $C_1$-$C_4$ alkyl.

Embodiment C17. A method of Embodiment C16 wherein A is phenyl or 2-thienyl, each optionally substituted with halogen.

Embodiment C18. A method of Embodiment C17 wherein A is 2-thienyl optionally substituted with halogen.

Embodiment C19. A method of any one of Embodiments C1 through C18 wherein R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl or $C_1$-$C_4$ haloalkoxy.

Embodiment C20. A method of Embodiment C19 wherein R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl or $C_1$-$C_4$ alkoxy.

Embodiment C21. A method of Embodiment C20 wherein R is Me.

Embodiment C22. A method of Embodiment C21 wherein R is phenyl, optionally substituted with $C_1$-$C_4$ alkyl.

Embodiment C23. A method of Embodiment C22 wherein R is 4-methylbenzene.

Embodiment C24. A method of any one of Embodiments C1 through C23 wherein B is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment C25. A method of Embodiment C24 wherein B is phenyl optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ di-alkylamino, cyano, nitro, $C_1$-$C_4$ alkoxy-carbonyl, phenyl or phenoxy.

Embodiment C26. A method of Embodiment C25 wherein B is phenyl optionally substituted with halogen, $C_1$-$C_4$ alkyl, $C_1$-$C_4$ alkenyl, $C_1$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

Embodiment C27. A method of Embodiment C26 wherein B is B1

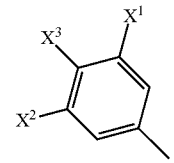

B1 wherein the bond projecting to the right is connected to the remainder of Formula IV or V;

$X^1$ is halogen, —$CF_3$, —$CF_2H$, —$OCF_3$, —$OCF_2H$, —$SCHF_2$ or —C≡CH;

$X^2$ is halogen, —$CF_3$, —$CF_2H$, —$OCF_3$, —$OCF_2H$, —$SCHF_2$ or —C≡CH; and $X^3$ is H or halogen.

Embodiment C28. A method of Embodiment C27 wherein $X^1$ is halogen, —$CF_3$, —$CF_2H$, —$OCF_3$ or —$OCF_2H$.

Embodiment C29. A method of Embodiment C28 wherein $X^1$ is halogen or —$CF_3$.

Embodiment C30. A method of Embodiment C29 wherein $X^1$ is halogen.

Embodiment C31. A method of Embodiment C30 wherein $X^1$ is Cl or Br.

Embodiment C32. A method of Embodiment C31 wherein $X^1$ is Cl.

Embodiment C33. A method of any one of Embodiments C27 through C32 wherein $X^2$ is halogen, —$CF_3$, —$CF_2H$, —$OCF_3$ or —$OCF_2H$.

Embodiment C34. A method of Embodiment C33 wherein $X^2$ is halogen or —$CF_3$.

Embodiment C35. A method of Embodiment C34 wherein $X^2$ is halogen.

Embodiment C36. A method of Embodiment C35 wherein $X^2$ is Cl or Br.

Embodiment C37. A method of Embodiment C36 wherein $X^2$ is Cl.

Embodiment C38. A method of any one of Embodiments C27 through C37 wherein $X^3$ is H, F, Cl or Br.

Embodiment C39. A method of Embodiment C38 wherein $X^3$ is H, F or Cl.

Embodiment C40. A method of Embodiment C39 wherein $X^3$ is H or Cl.

Embodiment C41. A method of Embodiment C40 wherein $X^3$ is H.

Embodiment C42. A method of Embodiment C40 wherein $X^3$ is Cl.

Embodiment C43. A method of any one of Embodiments C1 through C42 wherein the base used to form the secondary amine salt is a noncyclic secondary amine.

Embodiment C44. A method of any one of Embodiments C1 through C42 wherein the base used to form the secondary amine salt is a cyclic secondary amine.

Embodiment C45. A method of Embodiment C44 wherein the base used to form the secondary amine salt is piperidine, 2-methylpiperidine, 3-methylpiperidine, 4-methylpiperidine or morpholine.

Embodiment C46. A method of any one of Embodiments C1 through C45 wherein the acid used to form the salt is a weak or moderate acid.

Embodiment C47. A method of Embodiment C46 wherein the acid is an alkanoic acid.

Embodiment C48. A method of Embodiment C47 wherein the acid is formic, acetic or propionic acid.

Embodiment C49. A method of Embodiment C48 wherein the acid is acetic acid.

Embodiment C50. A method of any one of Embodiments C1 through C49 wherein the reaction temperature is from about −10° C. to about 110° C.

Embodiment C51. A method of Embodiment C50 wherein the reaction temperature is from about 25° C. to about 100° C.

Embodiment C52. A method of Embodiment C51 wherein the reaction temperature is from about 50° C. to about 90° C.

Embodiment C53. A method of any one of Embodiments C1 through C52 wherein the solvent comprises dimethylsulfoxide, N,N-dimethylformamide, N,N-dimethylacetamide, 1,2-dimethoxyethane, 1,2-diethoxyethane, dioxane, tetrahydrofuran or acetonitrile.

Embodiments of this invention, including any one of Embodiments A1 through A23, B1 through B37 and C1 through C53 above as well as any other embodiments described herein, can be combined in any manner, and the descriptions of variables in the embodiments pertain not only to the compounds of Formula I but also to the starting compounds and intermediate compounds useful for preparing the compounds of Formula I. In addition, embodiments of this invention, including any one of Embodiments A1 through A23, B1 through B37 and C1 through C53 above as well as any other embodiments described herein, and any combination thereof, pertain to the compositions and methods of the present invention.

Combinations of Embodiments A1 through A23, B1 through B37 and C1 through C53 are illustrated by:

Embodiment AA1. A compound of Formula I wherein
A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio; and
R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl or $C_1$-$C_4$ haloalkoxy.

Embodiment AA2. A compound of Embodiment AA1 wherein
A is phenyl, naphthalenyl, or a 5- or 6-membered heterocyclic ring, each ring or ring system optionally substituted with halogen; and
R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl or $C_1$-$C_4$ alkoxy.

Embodiment AA3. A compound of Formula I wherein
A is phenyl, optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy; and
R is $C_1$-$C_8$ alkyl.

Embodiment AA4. A compound of Embodiment AA3 wherein
A is phenyl optionally substituted with halogen; and
R is $CH_3$.

Embodiment AA5. A compound of Embodiment AA2 wherein
A is phenyl substituted with halogen at 3- and 5-positions or 2- and 5-positions; and
R is phenyl optionally substituted with $C_1$-$C_4$ alkyl.

Embodiment AA6. A compound of Embodiment AA2 wherein
A is phenyl, 2-thienyl, 3-thienyl or 3-pyridyl, each optionally substituted with halogen or $C_1$-$C_4$ alkyl; and
R is 4-methylbenzene.

Embodiment BB1. A method for preparing a compound of Formula I as described in the Summary of Invention wherein
A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio; and
R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl or $C_1$-$C_4$ haloalkoxy.

Embodiment BB2. A method of Embodiment BB1 wherein
A is phenyl, naphthalenyl, or a 5- or 6-membered heterocyclic ring, each ring or ring system optionally substituted with halogen;
R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl or $C_1$-$C_4$ alkoxy;

M is an alkali metal or $NH_4$; and
the acid is a weak or moderate acid.
Embodiment BB3. A method of Embodiment BB2
wherein
A is phenyl optionally substituted with halogen;
R is $CH_3$;
M is an alkali metal; and
the acid is an alkanoic acid.
Embodiment BB4. A method of Embodiment BB2
wherein
A is phenyl substituted with halogen at the 3- and 5-positions or at the 2- and 5-positions;
R is phenyl optionally substituted with $C_1$-$C_4$ alkyl;
M is Na or K;
the acid is formic, acetic or propionic acid;
the aqueous solvent mixture comprises an alcoholic solvent; and
the reaction temperature is from about 0° C. to about 75° C.
Embodiment BB5. A method of Embodiment BB2
wherein
A is phenyl, 2-thienyl, 3-thienyl or 3-pyridyl, each optionally substituted with halogen or $C_1$-$C_4$ alkyl;
R is 4-methylbenzene;
M is Na or K;
the acid is acetic acid;
the aqueous solvent mixture comprises ethanol; and
the reaction temperature is from about 10° C. to about 25° C.
Embodiment BB6. A method of Embodiment BB2
wherein
A is phenyl, 2-thienyl, 3-thienyl or 3-pyridyl, each optionally substituted with halogen or $C_1$-$C_4$ alkyl;
R is methyl or phenyl optionally substituted with $C_1$-$C_4$ alkyl;
M is Na or K; and
the acid is acetic acid.
Embodiment CC1. A method for preparing a compound of Formula IV as described in the Summary of Invention
wherein
A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio;
R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl or $C_1$-$C_4$ haloalkoxy; and
B is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.
Embodiment CC2. A method of Embodiment CC1
wherein
A is phenyl, naphthalenyl, or a 5- or 6-membered heterocyclic ring, each ring or ring system optionally substituted with halogen; and
R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl or $C_1$-$C_4$ alkoxy.
Embodiment CC3. A method of Embodiment CC2
wherein
B is B1 wherein
$X^1$ is halogen, $-CF_3$, $-CF_2H$, $-OCF_3$, $-OCF_2H$, $-SCHF_2$ or $-C\equiv CH$;
$X^2$ is halogen, $-CF_3$, $-CF_2H$, $-OCF_3$, $-OCF_2H$, $-SCHF_2$ or $-C\equiv CH$; and
$X^3$ is H or halogen.
Embodiment CC4. A method of Embodiment CC3
wherein
A is phenyl substituted with halogen at the 3- and 5-positions or at the 2- and 5-positions;
R is phenyl, optionally substituted with $C_1$-$C_4$ alkyl;
$X^1$ is halogen or $-CF_3$;
$X^2$ is halogen or $-CF_3$;
the base used to form the secondary amine salt is a cyclic secondary amine;
the acid is formic, acetic or propionic acid; and
the reaction temperature is from about 25° C. to about 100° C.
Embodiment CC5. A method of Embodiment CC3
wherein
A is phenyl substituted with halogen at the 3- and 5-positions or at the 2- and 5-positions;
R is $CH_3$;
$X^1$ is halogen or $-CF_3$;
$X^2$ is halogen or $-CF_3$;
the base used to form the secondary amine salt is a cyclic secondary amine;
the acid is formic, acetic or propionic acid; and
the reaction temperature is from about 25° C. to about 100° C.
Embodiment CC6. A method of Embodiment CC3
wherein
A is phenyl, 2-thienyl, 3-thienyl or 3-pyridyl, each ring optionally substituted with halogen or $C_1$-$C_4$ alkyl;
R is 4-methylbenzene;
the base used to form the secondary amine salt is piperidine, 2-methylpiperidine, 3-methylpiperidine, 4-methylpiperidine or morpholine;
the acid is acetic acid; and
the reaction temperature is from about 50° C. to about 90° C.
Embodiment CC7. A method of Embodiment CC6
wherein
A is phenyl or 2-thienyl, each optionally substituted with halogen or $C_1$-$C_4$ alkyl;
$X^1$ is Cl;
$X^2$ is Cl; and
$X^3$ is H.
Embodiment CC8. A method of Embodiment CC2
wherein
A is phenyl, 2-thienyl, 3-thienyl or 3-pyridyl, each ring optionally substituted with halogen; and
R is methyl or phenyl optionally substituted with $C_1$-$C_4$ alkyl.
Specific embodiments include compounds of Formula I selected from the group consisting of:
4-methylbenzenesulfonic acid 2-[(1E)-3-oxo-3-phenyl-1-propen-1-yl]hydrazide;
4-methylbenzenesulfonic acid 2-[(1E)-3-(3,5-difluorophenyl)-3-oxo-1-propen-1-yl]hydrazide; and
4-methylbenzenesulfonic acid 2-[(1E)-3-(2,5-difluorophenyl)-3-oxo-1-propen-1-yl]hydrazide.

In the following Schemes, the definitions of A, B, R and M are as defined above in the Summary of the Invention or any of Embodiments A1 through A23, B1 through B36 and C1 through C45, unless otherwise noted. As shown in Scheme 1, a compound of Formula IV can be prepared by treating a compound of Formula I with a compound of Formula V in a solvent such as dimethylsulfoxide, N,N-dimethylformamide, N,N-dimethylacetamide, 1,2-dimethoxyethane, 1,2-diethoxyethane, dioxane, tetrahydrofuran or acetonitrile, in the presence of a secondary amine salt formed by mixing an acid such as acetic acid, methanesulfonic acid, propionic acid, polyphosphoric acid or a mixture thereof, with a base such as piperdine, 2-methylpiperidine, 3-methylpiperidine, 4-methylpiperidine, morpholine or pyrrolidine. The reaction may be conducted at a temperature ranging from about 25° C. to about 100° C.; preferably about 50° C. to 90° C. and is allowed to proceed until completion. The reaction time can vary from about 1 to about 24 h.

Scheme 1

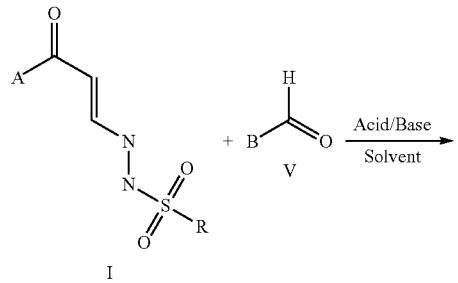

The compounds of Formula V are either commercially available or can be prepared by the methods described in Larock, R. C., *Comprehensive Organic Transformations: A Guide to Functional Group Preparations,* 2nd Ed., Wiley-VCH, New York, 1999. As shown in Scheme 2, a compound of Formula I can be prepared by mixing equimolar amounts of a compound of Formula III and a sulfonyl hydrazine derivative of Formula II in a solvent mixture of water and alcohol (e.g., ethanol, methanol, i-propanol or t-butanol). The ratio of alcohol to water can be from about 1:1 to about 90:1, preferably in the range of 1:1 to about 9:1. Excess alcohol relative to water can be used. Then an acid (e.g., acetic acid, propionic acid, methane sulfonic acid, trifluoro acetic acid or poylphosphoric acid) can be added to the reaction mixture. The amount of acid used is 1 equivalent to 2 equivalent; preferably about 1.5 equivalent based on the amount of the compound of Formula III. The reaction may be conducted at a temperature ranging from about −10° C. to about 110° C.; preferably about 20° C. to 30° C. and is allowed to proceed until completion. The reaction time can vary from about 1 to about 24 h.

Scheme 2

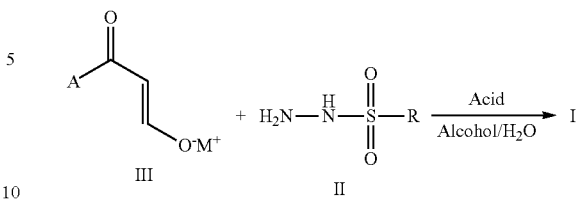

A compound of Formula III can be prepared from commercially available compounds of Formula 1 and Formula 2 as shown in Scheme 3. The Claisen condensation of the compound of Formula 1 and suitable alkyl or haloalkylformate of Formula 2 can be carried out in the presence of a base, such as metal alkoxide or hydride in a solvent such as diethyl ether, tetrahydrofuran, t-butylmethyl ether, N,N-dimethylformamide, toluene or ethanol. The reaction may be conducted at a temperature ranging from about 0° C. to about 110° C.; preferably from about 20° C. to about 60° C. and is allowed to proceed until completion. The reaction time can vary from about 1 to about 24 h. Alternatively, a compound of Formula III can be prepared by employing or modifying the methods known in the literature (e.g., *Organic Letters* 1999, 989-991; *Journal of Organic Chemistry* 1990, 55, 4767-4770 or *Journal of Medicinal Chemistry* 2003, 46, 5416-5427). The compound of Formula 1 are commercially available or can be prepared by the following methods described in Larock, R. C., *Comprehensive Organic Transformations: A Guide to Functional Group Preparations,* 2nd Ed., Wiley-VCH, New York, 1999.

Scheme 3

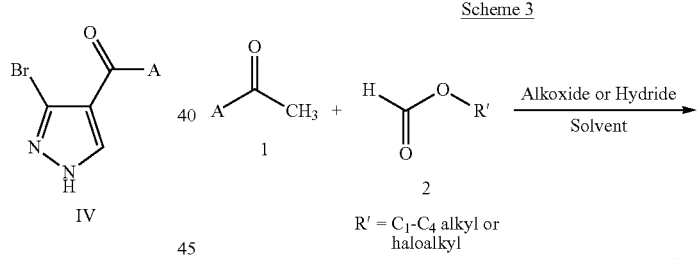

A compound of Formula III can also be prepared by the following procedures or modified procedures described in the literature (e.g. *Synthetic Communications,* 2000, 30 (15), 2759-2762) as shown in Scheme 4. A compound of Formula 1' is well documented in the literature, and can be prepared by the method described in *J. Organomet Chem.* 1980, C9-221. A compound of Formula 2' reacts with POCl₃ in a solvent such as dichloromethane or N,N-dimethylformamide at a temperature from about −5° C. to about 0° C. under an inert atmosphere to form Vilsmeier's reagent. After the reaction mixture is stirred at 0° C. for 5-10 min, the compound of Formula 1' is added and the mixture is stirred at room temperature for 2 to 4 h. The reaction mixture is then quenched with aqueous base (sodium hydroxide or potassium hydroxide) to produce the compound of Formula IIIa. The compound of Formula IIIa is then converted to the compound of Formula III using sodium methoxide or potassium butoxide.

Scheme 4

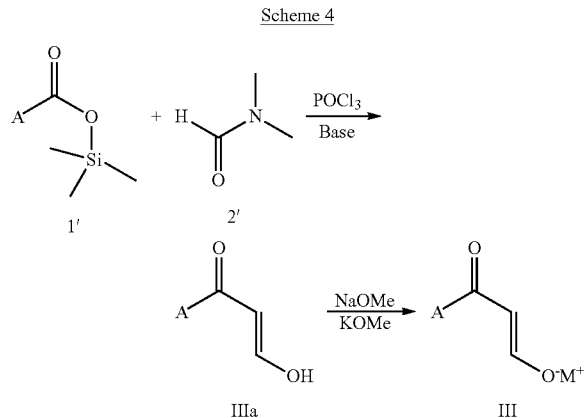

A compound of Formula II in Scheme 2 is either commercially available or can be prepared by known literature methods (e.g. *Synthesis*, 1980, 3, 244-5). As shown in Scheme 5, a compound of Formula II can be prepared by a two step procedure. Thus, first the reaction of a compound of Formula 3 and a compound of Formula 4 is conducted in the presence of a base such as pyridine, triethylamine or sodium carbonate in a solvent such as dichloromethane, acetonitrile or tetrahydrofuran at a temperature, typically between about 0° C. and about 70° C. under an inert atmosphere to produce a compound of Formula 5. Then the compound of Formula 5 is reacted with trifluoroacetic acid in a solvent such as dichloromethane or tetrahydrofuran at a temperature typically between about 0° C. and about 70° C. under an inert atmosphere to produce the compound of Formula II. The reaction time can vary from about 2 to about 14 h.

Scheme 5

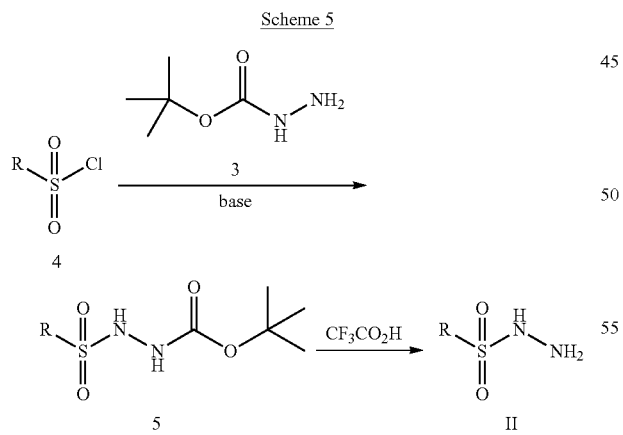

Alternatively, the compound of Formula II can also be prepared by condensation of the compound of Formula 4 and hydrazine 6 as shown in Scheme 6. Typical procedures for this type of condensation can be found, for example, in *Chemistry—A European Journal*, 2012, 18(6), 1582-1585. The compound of Formula 4 is added to hydrazine 6 in a solvent such as tetrahydrofuran or diethyl ether at a temperature between about 0° C. and about 20° C. under an inert atmosphere to produce the compound of Formula II.

Scheme 6

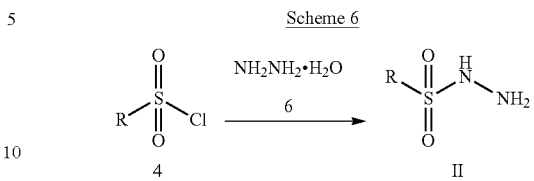

The compound of Formula 4 can be prepared from a compound of Formula 7 as shown in Scheme 7 by the methods described in the literature (e.g. *Synlett*, 2013, 24(16), 2165-2169 or *European Journal of Medicinal Chemistry* 2013, 60, 42-50). Thus, a compound of Formula 7 is reacted with sodium hypochlorite (NaOCl) in a solvent such as water, acetonitrile or dichloromethane at a temperature ranging from about −10° C. to about 20° C. to produce the compound of Formula 4. The reaction time can vary from about 1 to about 2 h.

Scheme 7

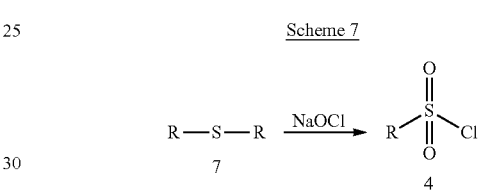

Alternatively, a compound of Formula 4 can be prepared from a commercially available bromide of Formula 8 as shown in Scheme 8 by a two step procedures described in the literature (e.g. *Synlett* 2013, 24(16), 2165-2169). Thus, a compound of Formula 8 is reacted with thiourea of Formula 9 in a solvent such as water, ethanol, methanol or i-propanol at a temperature ranging from about 20° C. to about 100° C. to provide a compound of Formula 10 as a salt. The reaction time can vary from about 1 to about 10 h. The salt of Formula 10 further reacts with sodium hypochlorite (NaOCl) in a solvent such as water, acetonitrile or dichloromethane at a temperature ranging from about −10° C. to about 20° C. to provide the compound of Formula 4. The reaction time can vary from about 1 to about 2 h.

Scheme 8

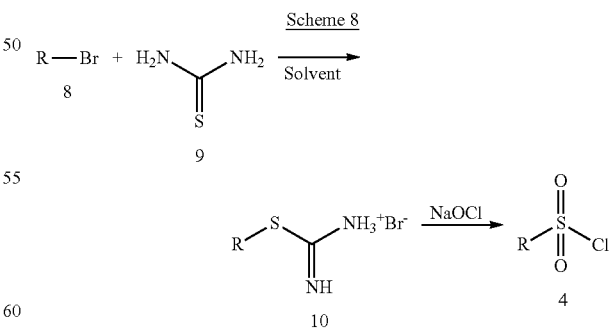

A compound of Formula 4 can also be prepared by the following methods described in the literature (e.g. *Tetrahedron* 2003, (59) 8, 1317-1325; *Synthesis* 2009, 14, 2321-2323 or WO 2013/037960) as shown in Scheme 9. Commercially available amine of Formula 11 reacts with NaNO$_2$ and hydrochloric acid to provide a diazonium salt as an intermediate, which further reacts with SO₂ in the presence of a metal salt such as CuCl or CuCl₂ in a solvent such as acetone or N,N-dimethylformamide at a temperature ranging from about 0° C. to about 20° C. to provide the compound of Formula 4. The reaction time can vary from about 1 to about 2 h.

Scheme 9

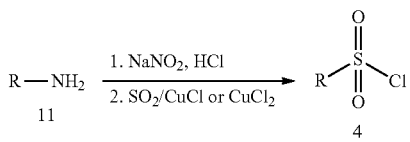

It is recognized by one skilled in the art that various functional groups can be converted into others to provide different compounds of Formula I. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula I may contain aromatic nitro groups, which can be reduced to amino groups, and then be converted via reactions well known in the art such as the Sandmeyer reaction, to various halides, providing compounds of Formula I. The above reactions can also in many cases be performed in alternate order.

It is recognized that some reagents and reaction conditions described above for preparing compounds of Formula I and IV may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds described in Schemes 1-9. One skilled in the art will also recognize that it may be necessary to perform a combination of the steps illustrated in the above schemes in an order other than that implied by the particular presented to prepare the compounds.

One skilled in the art will also recognize that compounds of Formula I, IV and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. ¹H NMR spectra are reported in ppm downfield from tetramethylsilane in DMSO at 400 MHZ unless otherwise noted; "s" means singlet, "d" means doublet, "t" means triplet, "q" means quartet, "m" means multiplet, "dd" means doublet of doublets, "dt" means doublet of triplets, and "bs" means broad singlet.

EXAMPLE 1

Preparation of [3-(3,5-dichlorophenyl)-1H-pyrazole-4-yl]phenylmethanone

Step A: Preparation of (2E)-3-Hydroxy-1-phenyl-2-propen-1-one sodium salt

A solution of acetophenone (300.0 g, 2.500 mol) and ethyl formate (212.7 g, 2.87 mol) in diethyl ether (1200 mL) was added dropwise to a solution of 25% sodium methoxide in methanol (600 mL) in diethyl ether (2400 mL) under N₂ at 0° C. over 30 minutes. After the addition, a precipitate was formed; and the reaction mixture was stirred at ambient temperature for 24 h. The precipitate was collected by filtration, washed with hexanes (2×100 mL) and dried under vacuum to provide the title compound as an off white solid (310 g).

¹H NMR δ 9.51 (d, 1H), 7.81 (m, 1H), 7.72 (m, 2H), 7.29 (m, 3H), 5.43 (d, 1H) and cis-isomer (30%).

Step B: Preparation of 4-methylbenzenesulfonic acid 2-[(1E)-3-oxo-3-phenyl-1-propen-1-yl]hydrazide A mixture of (2E)-3-hydroxy-1-phenyl-2-propen-1-one sodium salt (i.e. the compound obtained in Step A above) (1.5 g, 6.2 mmol) and p-toluene sulfonylhydrazide (337 g, 1.812 mol) was suspended in a solution of ethanol:water (3620:363 mL) and the mixture was cooled to 0° C. Acetic acid (150 mL) was added slowly. After the addition, all solids dissolved and a clear solution was formed. The reaction mixture was allowed to warm to ambient temperature and stirred for 16 h. The precipitate formed was collected by filtration, washed with hexanes (2×100 mL) and dried under vacuum to provide the title compound as a pale yellow solid (460 g).

¹H NMR δ 10.26 (bs, 1H), 7.64-7.92 (m, 5H), 7.39-7.95 (m, 5H), 7.36 (b, 1H), 5.85 (bs 1H), 2.33 (s, 3H).

Step C: Preparation of [3-(3,5-dichlorophenyl)-1H-pyrazole-4-yl]phenylmethanone

A mixture of 4-methylbenzenesulfonic acid 2-[(1E)-3-oxo-3-phenyl-1-propen-1-yl]hydrazide (i.e. the compound obtained in Step B above) (150 g, 0.474 mol) and 3,5 dichlorobenzaldehyde (83 g, 0.474 mol) was dissolved in N,N-dimethylformamide (1500 mL). The reaction mixture was cooled to 0° C. and piperidine (95 mL) was added dropwise. After the reaction mixture was stirred for 10 min, acetic acid (24 mL) was added dropwise and the mixture was heated at 90° C. for 3 h. The reaction mixture was allowed to cool to room temperature and ice water (3000 mL) was added. The precipitate formed was collected by filtration, washed with water (2×150 mL) and dried under vacuum to provide the product as a solid. The solid was further purified by recrystallization with 20% diethylether/pentane solution to provide the title compound as a pale yellow solid (120 g).
¹H NMR (CDCl₃, 400 MHz) δ 11.05 (bs, 1H), 7.94 (s, 1H), 7.78 (m, 2H), 7.57 (m, 3H), 7.44 (t, 2H), 7.33 (t, 1H).

EXAMPLE 2

Preparation of [3-(3,5-dichlorophenyl)-1H-pyrazol-4-yl](3,5-difluorophenyl)methanone Step A: Preparation of (2E)-1-(3,5-difluorophenyl)-3-hydroxy-2-propen-1-one sodium salt A solution of 3',5'-difluoroacetophenone (200 g, 1.28 mol) and ethyl formate (109 g, 1.47 mol) in diethyl ether (800 mL) was added dropwise to a solution of 25% sodium methoxide in methanol (400 mL) in diethyl ether (1600 mL) under N₂ at 0° C. over 30 minutes. After the addition, a precipitate formed, and the reaction mixture was stirred at ambient temperature for 24 h. The precipitate was collected by filtration, washed with hexanes (2×100 mL) and dried under vacuum to provide the title compound as an off-white solid (200 g).
¹H NMR δ 9.51 (d, 1H), 7.81 (m, 1H), 7.72 (m, 2H), 7.29 (m, 3H), 5.43 (d, 1H)+Z-isomer (30%).

Step B: Preparation of 4-methylbenzenesulfonic acid 2-[(1E)-3-(3,5-difluorophenyl)-3-oxo-1-propen-1-yl]hydrazide A mixture of (2E)-1-(3,5-difluorophenyl)-3-hydroxy-2-propen-1-one sodium salt (i.e. the compound obtained in Step A above) (200 g, 0.97 mol) and p-toluene sulfonylhydrazide (181 g, 0.97 mol) was suspended in a solution of ethanol:water (2000:240 mL) and the mixture was cooled to 0° C. Acetic acid (95 mL) was added slowly. After the addition, all solids dissolved and a clear solution was formed. The mixture was then allowed to warm to ambient temperature and stirred for 16 h. The precipitate formed was collected by filtration, washed with hexanes (2×100 mL) and dried under vacuum to provide the title compound as a pale yellow solid (190 g).
¹H NMR δ 10.02 (bs, 2H), 7.67-7.92 (m, 2H), 7.25-7.45 (m, 6H), 5.82 (bs 1H), 2.35 (d, 3H): mixture of (66.7% and 14.7%) E/Z isomers.

Step C: Preparation of [3-(3,5-dichlorophenyl)-1H-pyrazol-4-yl](3,5-difluorophenyl)methanone A mixture of 4-methylbenzenesulfonic acid 2-[(1E)-3-(3,5-difluorophenyl)-3-oxo-1-propen-1-yl]hydrazide (i.e. the compound obtained in Step B above)(170 g, 0.482 mol) and 3,5-dichlorobenzaldehyde (84.5 g, 0.482 mol) was dissolved in N,N-dimethylformamide (1700 mL). The reaction mixture was cooled to 0° C. and 3-methylpiperidine (114 mL) was added dropwise. After the reaction mixture was stirred for 10 min, acetic acid (25 mL) was added dropwise and the mixture was heated at 90° C. for 3 h. Then the reaction mixture was allowed to warm to room temperature, ice water (3100 mL) was added. The precipitate formed was collected by filtration, washed with water (2×150 mL) and dried under vacuum to provide the product as a solid. The solid was further purified by recrystallization with 30% diethylether/pentane to provide the title compound as a pale yellow solid (130 g, 76% yield).

¹H NMR (CDCl₃, 400 MHz) δ 10.05 (bs, 1H), 7.96 (s, 1H), 7.58 (d, 2H), 7.38 (s, 1H), 7.36 (t, 2H), 7.00 (t, 1H).

EXAMPLE 3

Preparation of [3-(3,5-dichlorophenyl)-1H-pyrazol-4-yl](2,5-difluorophenyl)methanone Step A: Preparation of (2E)-1-(2,5-difluorophenyl)-3-hydroxy-2-propen-1-one sodium salt A solution of 2',5'-difluoroacetophenone (500 g, 3.20 mol) and ethyl formate (272 g, 3.68 mol) in diethyl ether (2000 mL) was added dropwise to a solution of 25% sodium methoxide in methanol (1000 mL) in diethyl ether (2000 mL) under N₂ at 0° C. over 30 minutes. After the addition, a precipitate formed, and the reaction mixture was stirred at ambient temperature for 24 h. The precipitate was collected by filtration, washed with hexanes (3×100 mL) and dried under vacuum to provide the title compound as an off-white solid (580 g).
¹H NMR δ 9.50 (d, 1H), 7.31 (m, 1H), 7.22 (m, 2H), 4.78 (d, 1H)+isomer (50%).

Step B: Preparation of 4-methylbenzenesulfonic acid 2-[(1E)-3-(2,5-difluorophenyl)-3-oxo-1-propen-1-yl]hydrazide A mixture of (2E)-1-(2,5-difluorophenyl)-3-hydroxy-2-propen-1-one sodium salt (i.e. the compound obtained in Step A above) (580 g, 2.80 mol) and p-toluene sulfonylhydrazide (521 g, 2.80 mol) was suspended in a solution of ethanol: water (6780:678 mL) and the mixture was cooled to 0° C. Acetic acid (279 mL) was added slowly. After the addition, all solids dissolved and a clear solution was formed. The mixture was allowed to warm to ambient temperature and stirred for 16 h. The precipitate that formed was collected by filtration, washed with hexanes (2×200 mL) and dried under vaccum to provide a first crop of the product (600 g) as a pale yellow solid. The filtrate was concentrated under vacuum and the resulted solids were suspended in a solution of diethyl ether/hexanes (1/9) (1000 mL) and collected by filtration, washed with hexanes (2×100 mL) and dried to provide a second crop of the product (201 g). The analytical data were identical to the first crop.
¹H NMR δ 10.02 (bs, 1H), 9.44 (bs, 1H), 7.67 (m, 2H), 7.31-7.39 (m, 6H), 5.72 (bs 1H), 2.35 (bs, 3H): mixture of (64.9 and 33.6%) Z/E isomers.

Step C: Preparation of [3-(3,5-dichlorophenyl)-1H-pyrazol-4-yl](2,5-difluorophenyl)methanone A mixture of 4-methylbenzenesulfonic acid 2-[(1E)-3-(2,5-difluorophenyl)-3-oxo-1-propen-1-yl]hydrazide (i.e. the compound obtained in Step B above) (109 g, 0.511 mol) and 3,5-dichlorobenzaldehyde (89.5 g, 0.511 mol) was dissolved in 1,4-dioxane (1,620 mL). The reaction mixture was cooled to 0° C. and piperidine (109 mL) was added dropwise. After the reaction mixture was stirred for 10 min, acetic acid (29 mL) was added dropwise and the mixture was heated at 90° C. for 3 h. Then the reaction mixture was cooled to room temperature and ice water (3200 mL) was added. The precipitate formed was collected by filtration, washed with water (2×150 mL) and dried under vacuum to provide the product as a solid. The solid was further purified by recrystallization with 20% diethyl ether/pentane to provide the title compound as a pale yellow solid (150 g, 83% yield).

$^1$H NMR (CDCl$_3$, 400 MHz) δ 7.96 (s, 1H), 7.56 (d, 2H), 7.34 (s, 1H), 7.20 (m, 1H), 7.12 (m, 1H), 6.99 (m, 1H).

By the procedures described herein together with methods known in the art, the following compounds of Tables 1, 1A to 1C, Tables 2 to 60 can be prepared. The following abbreviations are used in the Tables which follow: t means tertiary, s means secondary, n means normal, i means iso, c means cyclo, Me means methyl, Et means ethyl, Pr means propyl, Bu means butyl, i-Pr means isopropyl, Bu means butyl, c-Pr cyclopropyl, c-Bu means cyclobutyl, Ph means phenyl, OMe means methoxy, OEt means ethoxy, SEt means ethylthio, NHMe methylamino, —CN means cyano, —NO$_2$ means nitro, S(O)Me means methylsulfinyl, and S(O)$_2$Me means methylsulfonyl.

TABLE A

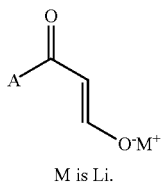

M is Li.

| A | A | A |
|---|---|---|
| 2-Cl—Ph | 2-Cl-3-F—Ph | 2,6-di-Cl—Ph |
| 4-Cl—Ph | 3-Cl-5-F—Ph | 3,4-di-F—Ph |
| 3-Cl—Ph | 3-Cl-6-F—Ph | 3,5-di-F—Ph |
| 3-OCHF$_2$—Ph | 4-Cl-3-F—Ph | 3,4-di-Cl—Ph |
| 3-CH$_2$CCl$_2$F—Ph | 2-Br-3-Cl—Ph | 3,5-di-Cl—Ph |
| thiophen-2-yl | 2-Br-4-Cl—Ph | 2,3-di-Br—Ph |
| 2,5-di-Cl—Ph | 2-Br-5-Cl—Ph | 2,3,4,5-tetra-Cl—Ph |
| 2,4-di-Cl—Ph | 2-Br-6-Cl—Ph | 2,3,5,6-tetra-Cl—Ph |
| 3-NMe2—Ph | 3-Br-2-Cl—Ph | 2,3,4,6-tetra-Cl—Ph |
| 2-Cl—Ph | 3-Br-4-Cl—Ph | 2,3,4,5,6-penta-Cl—Ph |
| furan-2-yl | 3-Br-5-Cl—Ph | 2,4,6-tri-Br—Ph |
| 2-naphthyl | 3-Br-6-Cl—Ph | 2,3,5-tri-Br—Ph |
| 1-naphthyl | 4-Br-2-Cl—Ph | 2,3,4-tri-Br—Ph |
| pyridin-3-yl | 4-Br-3-Cl—Ph | 5-Cl-thiophen-2-yl |
| 5-Cl-thiophen-2-yl | 2-Br-3-I—Ph | 1-Me-3,5-di-Cl-pyrazol-4-yl |
| 3,5-di-F—Ph | 2-Br-4-I—Ph | 1-Me-5-Cl-pyrazol-4-yl |
| 3-OPh—Ph | 2-Br-5-I—Ph | 2,6-di-Cl-pyridin-4-yl |
| 2,6-di-Cl-pyridin-4-yl | 2-Br-6-I—Ph | thiophen-3-yl |
| 2-F—Ph | 3-Br-2-I—Ph | 3-F-pyridin-2-yl |
| 3-F—Ph | 3-Br-4-I—Ph | 4-Br-3,5-di-F—Ph |
| 4-F—Ph | 2-CN—Ph | 4-F-3-OMe—Ph |
| 2-Br—Ph | 3-CN—Ph | 3-F-4-OMe—Ph |
| 3-Br—Ph | 4-CN—Ph | 4-Cl-3-OMe—Ph |
| 4-Br—Ph | 3-NO$_2$—Ph | 3-Cl-4-OMe—Ph |
| 2-Cl-3-NO$_2$—Ph | 4-NO$_2$—Ph | 4-Br-3-OMe—Ph |
| 2-Cl-4-NO$_2$—Ph | 3-CF$_3$—Ph | 4-F-3,5-di-OMe—Ph |
| 4-Cl-2-NO$_2$—Ph | 4-CF$_3$—Ph | 3-F-5-CF$_3$—Ph |
| 5-Cl-2-NO$_2$—Ph | 3-CHF$_2$—Ph | 3-Cl-5-CF$_3$—Ph |
| 4-Cl-3-OPh—Ph | 4-CHF$_2$—Ph | 3,5-di-CF$_3$—Ph |
| 4-OMe-3-NO$_2$—Ph | 3-CH$_2$Cl—Ph | 2,4-(CF$_3$)$_2$—Ph |
| 2,3,6-tri-F—Ph | 3-CH$_2$Br—Ph | 4-F-3-CN—Ph |
| 2,3,4-tri-F—Ph | 3-CH$_2$I—Ph | 3,5-di-CN—Ph |
| 2,3,5-tri-F—Ph | 3-CCl$_3$—Ph | 2-CO$_2$Me—Ph |
| 2,4,6-tri-F—Ph | 3-CH$_2$F—Ph | 3-CO$_2$Me—Ph |
| 2,3,4,5,6-penta-F—Ph | 3-CHCl$_2$—Ph | 4-CO$_2$Me—Ph |
| 2-Br-3-F—Ph | 3-CH$_2$CH$_2$F—Ph | 4-F-3-CO$_2$Me—Ph |
| 2-Br-5-F—Ph | 3-CF$_2$Cl—Ph | 4-Cl-3-CO$_2$Me—Ph |
| 2-Br-6-F—Ph | 3-CH$_2$CF$_3$—Ph | 2-Ph—Ph |
| 3-Br-2-F—Ph | 4-CH$_2$Cl—Ph | 3-Br-5-I—Ph |
| 3-Br-5-F—Ph | 4-CH$_2$Br—Ph | 2,4-di-Br—Ph |
| 4-Br-2-F—Ph | 4-CH$_2$I—Ph | 2,5-di-Br—Ph |
| 4-Br-3-F—Ph | 4-CCl$_3$—Ph | 2,6-di-Br—Ph |
| 2-F-3-I—Ph | 4-CH$_2$F—Ph | 3,4-di-Br—Ph |
| 2-F-4-I—Ph | 4-CHCl$_2$—Ph | 3,5-di-Br—Ph |
| 2-F-5-I—Ph | 3,4,5-tri-OEt—Ph | 2,3-di-Me—Ph |
| 2-F-6-I—Ph | 3,4,5-tri-OMe—Ph | 2,4-di-Me—Ph |
| 3-F-4-I—Ph | 2,4-di-Cl-5-F—Ph | 2,5-di-Me—Ph |
| 3-F-6-I—Ph | 2,3,4,5-tetra-F—Ph | 2,6-di-Me—Ph |
| 4-F-2-I—Ph | 2,3,5,6-tetra-F—Ph | 3,4-di-Me—Ph |
| 4-F-3-I—Ph | 2,3,4,6-tetra-F—Ph | 3,5-di-Me—Ph |

TABLE A-continued

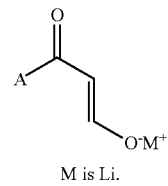

M is Li.

| A | A | A |
|---|---|---|
| 2-Cl-3,4-di-F—Ph | 2,3,6-tri-I—Ph | 2-F-4-Cl—Ph |
| 2-Cl-3,5-di-F—Ph | 3-Br-6-I—Ph | 2-F-5-Cl—Ph |
| 2-Cl-3,6-di-F—Ph | 4-Br-2-I—Ph | 2-F-6-Cl—Ph |
| 2-Cl-4,5-di-F—Ph | 4-Br-3-I—Ph | 3-F-4-Cl—Ph |
| 2-Cl-4,6-di-F—Ph | 3-Cl-4,5-di-F—Ph | 3-Cl-4-F—Ph |
| 2-Cl-5,6-di-F—Ph | 4-Cl-2,3-di-F—Ph | 2-Cl-4-F—Ph |
| 3-Cl-2,4-di-F—Ph | 2-Cl-5,6-di-F—Ph | 2-Cl-6-F—Ph |
| 3-Cl-2,5-di-F—Ph | 3-Cl-4,5-di-F—Ph | 2-Br-4-F—Ph |
| 2-I—Ph | 3-Cl-4,6-di-F—Ph | 3-Br-4-F—Ph |
| 3-I—Ph | 4-Cl-3,5-di-F—Ph | 2-F-5-Br—Ph |
| 3-I—Ph | 3,4-di-Cl-2-F—Ph | 4-Me-2-NO$_2$—Ph |
| 2-Me—Ph | 3,5-di-Cl-2-F—Ph | 2-OMe-4-Cl—Ph |
| 3-Me—Ph | 3,4-di-Cl-2-F—Ph | 2-Cl-4-NO$_2$—Ph |
| 4-Me—Ph | 2,5-di-Cl-6-F—Ph | 3,4,5-tri-Br—Ph |
| 2-Et—Ph | 2,4-di-Cl-6-F—Ph | 2,4,5-tri-Br—Ph |
| 3-Et—Ph | 2,5-di-Cl-3-F—Ph | 2,3,6-tri-Br—Ph |
| 4-Et—Ph | 2,6-di-Cl-3-F—Ph | 2,4-di-I—Ph |
| 2-Pr—Ph | 3,4-di-Cl-5-F—Ph | 2,3,5-tri-I—Ph |
| 3-Pr—Ph | 2,3-di-Cl-4-F—Ph | 2,6-di-I—Ph |
| 4-Pr—Ph | 2,5-di-Cl-4-F—Ph | 2,5-di-I—Ph |
| 3-i-Pr—Ph | 2,6-di-Cl-4-F—Ph | 2-Cl-3,4,5-tri-F—Ph |
| 3-i-Pr—Ph | 3,5-di-Cl-4-F—Ph | 2-Cl-3,4,6-tri-F—Ph |
| 4-Bu—Ph | 2,3-di-Cl-5-F—Ph | 2-Cl-3,5,6-tri-F—Ph |
| 3-t-Bu—Ph | 2,3-di-Cl-6-F—Ph | 3-Cl-4,5,6-tri-F—Ph |
| 4-t-Bu—Ph | 2-Br-3,4-di-F—Ph | 2-Cl-3,4,5,6-tetra-F—Ph |
| 3-i-Bu—Ph | 2-Br-3,5-di-F—Ph | 3-Cl-2,4,5,6-tetra-F—Ph |
| 3-OMe—Ph | 2-Br-3,6-di-F—Ph | 2,4-Cl$_2$-3,4,6-tri-F—Ph |
| 4-OMe—Ph | 3-Br-2,5-di-F—Ph | 3,4,5-tri-Cl-2,6-di-F—Ph |
| 2-OMe—Ph | 4-CH$_2$CH$_2$F—Ph | 3-Ph—Ph |
| 3-OEt—Ph | 4-CF$_2$Cl—Ph | 4-Ph—Ph |
| 3-O(i-Pr)—Ph | 4-CH$_2$CF$_3$—Ph | 4-CF$_3$-3-Ph—Ph |
| 4-O(i-Pr)—Ph | 3-OCHF$_2$—Ph | 4-F-3-Ph—Ph |
| 2,4,5-tri-F—Ph | 4-OCHF$_2$—Ph | 2-OPh—Ph |
| 2,4,5-tri-Cl—Ph | 3-OCF$_3$—Ph | 4-F-3-OPh—Ph |
| 2,4,6-tri-Cl—Ph | 4-OCF$_3$—Ph | 4-Cl-3-OPh—Ph |
| 2,3,5-tri-Cl—Ph | 3-NMe2—Ph | 3-Cl-4-OPh—Ph |
| 2,3,4-tri-Cl—Ph | 4-NMe2—Ph | 4-Br-2,3,5-tri-F—Ph |
| 2,3,6-tri-Cl—Ph | 3-OCH$_2$CF$_3$—Ph | 4-Br-2,3,6-tri-F—Ph |
| 3,4,5-tri-F—Ph | 4-OCH$_2$CF$_3$—Ph | Thiazol-2-yl |
| 3,4,5-tri-Cl—Ph | 2,3-di-F—Ph | Pyrimidin-2-yl |
| 2,3,5-tri-I—Ph | 2,4-di-F—Ph | 3-CF$_3$-isoxazol-1-yl |
| 2,3,4-tri-I—Ph | 2,5-di-F—Ph | 3-F-thiazol-2-yl |
| 2-Cl-3-F—Ph | 2,6-di-F—Ph | 2,5-di-F-thiophen-3-yl |
| 2-Cl-4-F—Ph | 2,3-di-Cl—Ph | 3-CF$_3$-1-Me-pyrazol-2-yl |
| 2-Cl-5-F—Ph | 2,4-di-Cl—Ph | 3-Br-4,5-di-F—Ph |
| 2-Cl-6-F—Ph | 2,5-di-Cl—Ph | 3-Cl-2,6-di-F—Ph |

The present disclosure also includes Tables 1A through 1C, each of which is constructed the same as Table A above, except that the row heading in Table A (i.e. "M is Li.") is replaced with the respective row headings shown below. For Example, in Table 1A, the row heading is "M is Na.", and A is as defined in Table A above.

| Table | Row Heading |
|---|---|
| 1A | M is Na |
| 1B | M is K |
| 1C | M is NH$_4$ |

TABLE 2

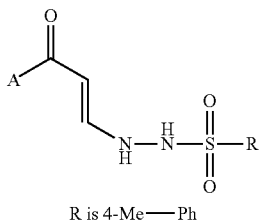

R is 4-Me—Ph

| A | A | A |
|---|---|---|
| 2-Cl—Ph | 2-Cl-3-F—Ph | 2,6-di-Cl—Ph |
| 4-Cl—Ph | 3-Cl-5-F—Ph | 3,4-di-F—Ph |
| 3-Cl—Ph | 3-Cl-6-F—Ph | 3,5-di-F—Ph |
| 3-OCHF$_2$—Ph | 4-Cl-3-F—Ph | 3,4-di-Cl—Ph |
| 3-CH$_2$CCl$_2$F—Ph | 2-Br-3-Cl—Ph | 3,5-di-Cl—Ph |
| thiophen-2-yl | 2-Br-4-Cl—Ph | 2,3-di-Br—Ph |
| 2,5-di-Cl—Ph | 2-Br-5-Cl—Ph | 2,3,4,5-tetra-Cl—Ph |
| 2,4-di-Cl—Ph | 2-Br-6-Cl—Ph | 2,3,5,6-tetra-Cl—Ph |
| 3-NMe2—Ph | 3-Br-2-Cl—Ph | 2,3,4,6-tetra-Cl—Ph |
| 2-Cl—Ph | 3-Br-4-Cl—Ph | 2,3,4,5,6-penta-Cl—Ph |
| furan-2-yl | 3-Br-5-Cl—Ph | 2,4,6-tri-Br—Ph |
| 2-naphthyl | 3-Br-6-Cl—Ph | 2,3,5-tri-Br—Ph |
| 1-naphthyl | 4-Br-2-Cl—Ph | 2,3,4-tri-Br—Ph |
| pyridin-3-yl | 4-Br-3-Cl—Ph | 5-Cl-thiophen-2-yl |
| 5-Cl-thiophen-2-yl | 2-Br-3-I—Ph | 1-Me-3,5-di-Cl-pyrazol-4-yl |
| 3,5-di-F—Ph | 2-Br-4-I—Ph | 1-Me-5-Cl-pyrazol-4-yl |
| 3-OPh—Ph | 2-Br-5-I—Ph | 2,6-di-Cl-pyridin-4-yl |
| 2,6-di-Cl-pyridin-4-yl | 2-Br-6-I—Ph | thiophen-3-yl |
| 2-F—Ph | 3-Br-2-I—Ph | 3-F-pyridin-2-yl |
| 3-F—Ph | 3-Br-4-I—Ph | 4-Br-3,5-di-F—Ph |
| 4-F—Ph | 2-CN—Ph | 4-F-3-OMe—Ph |
| 2-Br—Ph | 3-CN—Ph | 3-F-4-OMe—Ph |
| 3-Br—Ph | 4-CN—Ph | 4-Cl-3-OMe—Ph |
| 4-Br—Ph | 3-NO$_2$—Ph | 3-Cl-4-OMe—Ph |
| 2-Cl-3-NO$_2$—Ph | 4-NO$_2$—Ph | 4-Br-3-OMe—Ph |
| 2-Cl-4-NO$_2$—Ph | 3-CF$_3$—Ph | 4-F-3,5-di-OMe—Ph |
| 4-Cl-2-NO$_2$—Ph | 4-CF$_3$—Ph | 3-F-5-CF$_3$—Ph |
| 5-Cl-2-NO$_2$—Ph | 3-CHF$_2$—Ph | 3-Cl-5-CF$_3$—Ph |
| 4-Cl-3-OPh—Ph | 4-CHF$_2$—Ph | 3,5-di-CF$_3$—Ph |
| 4-OMe-3-NO$_2$—Ph | 3-CH$_2$Cl—Ph | 2,4-(CF$_3$)$_2$—Ph |
| 2,3,6-tri-F—Ph | 3-CH$_2$Br—Ph | 4-F-3-CN—Ph |
| 2,3,4-tri-F—Ph | 3-CH$_2$I—Ph | 3,5-di-CN—Ph |
| 2,3,5-tri-F—Ph | 3-CCl$_3$—Ph | 2-CO$_2$Me—Ph |
| 2,4,6-tri-F—Ph | 3-CH$_2$F—Ph | 3-CO$_2$Me—Ph |
| 2,3,4,5,6-penta-F—Ph | 3-CHCl$_2$—Ph | 4-CO$_2$Me—Ph |
| 2-Br-3-F—Ph | 3-CH$_2$CH$_2$F—Ph | 4-F-3-CO$_2$Me—Ph |
| 2-Br-5-F—Ph | 3-CF$_2$Cl—Ph | 4-Cl-3-CO$_2$Me—Ph |
| 2-Br-6-F—Ph | 3-CH$_2$CF$_3$—Ph | 2-Ph—Ph |
| 3-Br-2-F—Ph | 4-CH$_2$Cl—Ph | 3-Br-5-I—Ph |
| 3-Br-5-F—Ph | 4-CH$_2$Br—Ph | 2,4-di-Br—Ph |
| 4-Br-2-F—Ph | 4-CH$_2$I—Ph | 2,5-di-Br—Ph |
| 4-Br-3-F—Ph | 4-CCl$_3$—Ph | 2,6-di-Br—Ph |
| 2-F-3-I—Ph | 4-CH$_2$F—Ph | 3,4-di-Br—Ph |
| 2-F-4-I—Ph | 4-CHCl$_2$—Ph | 3,5-di-Br—Ph |
| 2-F-5-I—Ph | 3,4,5-tri-OEt—Ph | 2,3-di-Me—Ph |
| 2-F-6-I—Ph | 3,4,5-tri-OMe—Ph | 2,4-di-Me—Ph |
| 3-F-4-I—Ph | 2,4-di-Cl-5-F—Ph | 2,5-di-Me—Ph |
| 3-F-6-I—Ph | 2,3,4,5-tetra-F—Ph | 2,6-di-Me—Ph |
| 4-F-2-I—Ph | 2,3,5,6-tetra-F—Ph | 3,4-di-Me—Ph |
| 4-F-3-I—Ph | 2,3,4,6-tetra-F—Ph | 3,5-di-Me—Ph |
| 2-Cl-3,4-di-F—Ph | 2,3,6-tri-I—Ph | 2-F-4-O—Ph |
| 2-Cl-3,5-di-F—Ph | 3-Br-6-I—Ph | 2-F-5-Cl—Ph |
| 2-Cl-3,6-di-F—Ph | 4-Br-2-I—Ph | 2-F-6-O—Ph |
| 2-Cl-4,5-di-F—Ph | 4-Br-3-I—Ph | 3-F-4-Cl—Ph |
| 2-Cl-4,6-di-F—Ph | 3-Cl-4,5-di-F—Ph | 3-Cl-4-F—Ph |
| 2-Cl-5,6-di-F—Ph | 4-Cl-2,3-di-F—Ph | 2-Cl-4-F—Ph |
| 3-Cl-2,4-di-F—Ph | 2-Cl-5,6-di-F—Ph | 2-Cl-6-F—Ph |
| 3-Cl-2,5-di-F—Ph | 3-Cl-4,5-di-F—Ph | 2-Br-4-F—Ph |
| 2-I—Ph | 3-Cl-4,6-di-F—Ph | 3-Br-4-F—Ph |
| 3-I—Ph | 4-Cl-3,5-di-F—Ph | 2-F-5-Br—Ph |
| 3-I—Ph | 3,4-di-Cl-2-F—Ph | 4-Me-2-NO$_2$—Ph |
| 2-Me—Ph | 3,5-di-Cl-2-F—Ph | 2-OMe-4-Cl—Ph |
| 3-Me—Ph | 3,4-di-Cl-2-F—Ph | 2-Cl-4-NO$_2$—Ph |
| 4-Me—Ph | 2,5-di-Cl-6-F—Ph | 3,4,5-tri-Br—Ph |
| 2-Et—Ph | 2,4-di-Cl-6-F—Ph | 2,4,5-tri-Br—Ph |
| 3-Et—Ph | 2,5-di-Cl-3-F—Ph | 2,3,6-tri-Br—Ph |

TABLE 2-continued

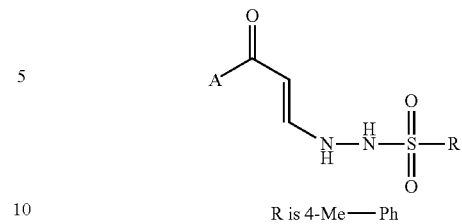

R is 4-Me—Ph

| A | A | A |
|---|---|---|
| 4-Et—Ph | 2,6-di-Cl-3-F—Ph | 2,4-di-I—Ph |
| 2-Pr—Ph | 3,4-di-Cl-5-F—Ph | 2,3,5-tri-I—Ph |
| 3-Pr—Ph | 2,3-di-Cl-4-F—Ph | 2,6-di-I—Ph |
| 4-Pr—Ph | 2,5-di-Cl-4-F—Ph | 2,5-di-I—Ph |
| 3-i-Pr—Ph | 2,6-di-Cl-4-F—Ph | 2-Cl-3,4,5-tri-F—Ph |
| 3-i-Pr—Ph | 3,5-di-Cl-4-F—Ph | 2-Cl-3,4,6-tri-F—Ph |
| 4-Bu—Ph | 2,3-di-Cl-5-F—Ph | 2-Cl-3,5,6-tri-F—Ph |
| 3-t-Bu—Ph | 2,3-di-Cl-6-F—Ph | 3-Cl-4,5,6-tri-F—Ph |
| 4-t-Bu—Ph | 2-Br-3,4-di-F—Ph | 2-Cl-3,4,5,6-tetra-F—Ph |
| 3-i-Bu—Ph | 2-Br-3,5-di-F—Ph | 3-Cl-2,4,5,6-tetra-F—Ph |
| 3-OMe—Ph | 2-Br-3,6-di-F—Ph | 2,4-Cl$_2$-3,4,6-tri-F—Ph |
| 4-OMe—Ph | 3-Br-2,5-di-F—Ph | 3,4,5-tri-Cl-2,6-di-F—Ph |
| 2-OMe—Ph | 4-CH$_2$CH$_2$F—Ph | 3-Ph—Ph |
| 3-OEt—Ph | 4-CF$_2$Cl—Ph | 4-Ph—Ph |
| 3-O(i-Pr)—Ph | 4-CH$_2$CF$_3$—Ph | 4-CF$_3$-3-Ph—Ph |
| 4-O(i-Pr)—Ph | 3-OCHF$_2$—Ph | 4-F-3-Ph—Ph |
| 2,4,5-tri-Cl—Ph | 4-OCHF$_2$—Ph | 2-OPh—Ph |
| 2,4,5-tri-Cl—Ph | 3-OCF$_3$—Ph | 4-F-3-OPh—Ph |
| 2,4,6-tri-Cl—Ph | 4-OCF$_3$—Ph | 4-Cl-3-OPh—Ph |
| 2,3,5-tri-Cl—Ph | 3-NMe2—Ph | 3-Cl-4-OPh—Ph |
| 2,3,4-tri-Cl—Ph | 4-NMe2—Ph | 4-Br-2,3,5-tri-F—Ph |
| 2,3,6-tri-Cl—Ph | 3-OCH$_2$CF$_3$—Ph | 4-Br-2,3,6-tri-F—Ph |
| 3,4,5-tri-F—Ph | 4-OCH$_2$CF$_3$—Ph | Thiazol-2-yl |
| 3,4,5-tri-Cl—Ph | 2,3-di-F—Ph | Pyrimidin-2-yl |
| 2,3,5-tri-I—Ph | 2,4-di-F—Ph | 3-CF$_3$-isoxazol-1-yl |
| 2,3,4-tri-I—Ph | 2,5-di-F—Ph | 3-F-thiazol-2-yl |
| 2-Cl-3-F—Ph | 2,6-di-F—Ph | 2,5-di-F-thiophen-3-yl |
| 2-Cl-4-F—Ph | 2,3-di-Cl—Ph | 3-CF$_3$-1-Me-pyrazol-2-yl |
| 2-Cl-5-F—Ph | 2,4-di-Cl—Ph | 3-Br-4,5-di-F—Ph |
| 2-Cl-6-F—Ph | 2,5-di-Cl—Ph | 3-Cl-2,6-di-F—Ph |

Tables 3 through 59 are constructed the same as Table 2 above, except that the row heading in Table 2 (i.e. "R is 4-Me-Ph.") is replaced with the respective row heading shown below. For example, in Table 3, the row heading is "R is 3-Me-Ph." and A is defined as in Table 2 above.

| Table | Row Heading: R is |
|---|---|
| 3 | 3-Me—Ph |
| 4 | 2-Me—Ph |
| 5 | 4-OMe—Ph |
| 6 | 3-OMe—Ph |
| 7 | 2-OMe—Ph |
| 8 | 4-NO$_2$—Ph |
| 9 | 3-NO$_2$—Ph |
| 10 | 2-NO$_2$—Ph |
| 11 | 4-OCHF$_2$—Ph |
| 12 | 3-OCHF$_2$—Ph |
| 13 | 2-OCHF$_2$—Ph |
| 14 | Ph |
| 15 | Me |
| 16 | Et |
| 17 | n-hexyl |
| 18 | t-Bu |
| 19 | —CH$_2$—Ph |
| 20 | 4-Cl—Ph |
| 21 | 3-Cl—Ph |
| 22 | 2-Cl—Ph |
| 23 | 3-CF$_3$—Ph |
| 24 | 4-CF$_3$—Ph |
| 25 | 2-CF$_3$—Ph |
| 26 | 4-F—Ph |

-continued

| Table | Row Heading: R is |
|---|---|
| 27 | 3-F—Ph |
| 28 | 2-F—Ph |
| 29 | 2,4-di-Cl—Ph |
| 30 | 2,4-Me—Ph |
| 31 | 2,4-di-F—Ph |
| 32 | 2-naphthyl |
| 33 | 1-naphthyl |
| 34 | 2-thiophen-1-yl |
| 35 | 2-furan-1-yl |
| 36 | 5-Cl-2-thiophen-1-yl |
| 37 | 3-pyridinyl |
| 38 | 2-Ph—Ph |
| 39 | 3-Ph—Ph |
| 40 | 4-Ph—Ph |
| 41 | —CH$_2$OCH$_2$CH$_3$ |
| 42 | 4-OPh—Ph |
| 43 | 3-OPh—Ph |
| 44 | 2-OPh—Ph |
| 45 | 2,5-di-OMe—Ph |
| 46 | 2-OMe-5-Cl—Ph |
| 47 | 2,4,5-tri-Me—Ph |
| 48 | —CH$_2$CH$_2$CH$_3$ |
| 49 | CH$_2$-4-Me—Ph |
| 50 | 2,5-di-Me-thiazol-1-yl |
| 51 | 2,5-di-Me-isoxazol-1-yl |
| 52 | —CH$_2$CH$_2$CN |
| 53 | CH$_2$-4-Cl—Ph |
| 54 | 2-pyridinyl |
| 55 | 4-pyridinyl |
| 56 | 2-pyrimidinyl |
| 57 | 3-pyrimidinyl |
| 58 | 4-pyrimidinyl |
| 59 | 3,4-di-Cl—Ph |

What is claimed is:

1. A compound selected from Formula I, N-oxides and salts thereof,

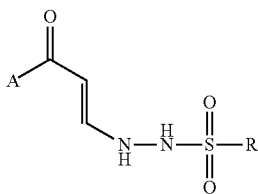

I wherein
A is phenyl substituted with halogen, $C_2$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy; or
A is a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy;R is $C_1$-$C_8$ alkyl optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy; and
R is $C_1$-$C_8$ alkyl optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy; or
R is phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy.

2. The compound of claim 1 wherein
A is phenyl substituted with halogen, $C_2$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio; and
R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl or $C_1$-$C_4$ haloalkoxy.

3. The compound of claim 2 wherein
A is phenyl substituted with halogen; and
R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl or $C_1$-$C_4$ alkoxy.

4. The compound of claim 1 wherein
A is phenyl substituted with halogen, $C_2$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy; and
R is $C_1$-$C_8$ alkyl.

5. The compound of claim 4 wherein
A is phenyl substituted with halogen; and
R is $CH_3$.

6. The compound of claim 3 wherein
A is phenyl substituted with halogen at 3- and 5-positions or 2- and 5-positions; and
R is phenyl optionally substituted with $C_1$-$C_4$ alkyl.

7. The compound of claim 2 wherein
A is phenyl substituted with halogen, $C_2$-$C_4$ alkyl and
R is 4-methylbenzene.

8. A method for preparing a compound of Formula I

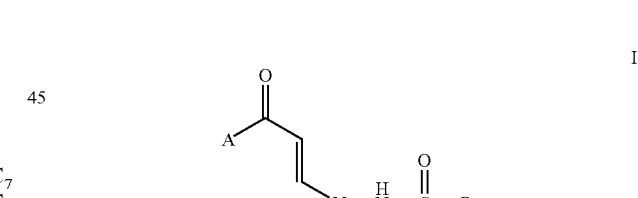

I wherein
A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy; and
R is $C_1$-$C_8$ alkyl optionally substituted with halogen, $C_1$-$C_4$ alkyl, $C_2$-$C_4$ alkenyl, $C_2$-$C_4$ alkynyl, $C_1$-$C_4$ alkoxy, haloalkyl, $C_1$-$C_4$ haloalkoxy, cyano, nitro, phenyl or phenoxy; or
R is phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy;
comprising the step of reacting a compound of Formula II

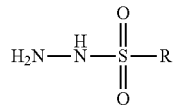

II wherein
- R is $C_1$-$C_8$ alkyl optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy; or
- R is phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy;

with an aroyl enolate salt of Formula III

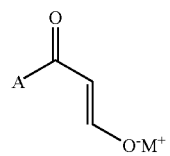

III wherein
- M is an alkali metal or $NH_4$;
- A is phenyl, naphthalenyl, or a 5- or 6- membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy;

in the presence of an acid in an aqueous solvent mixture.

9. The method of claim 8 wherein
- A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio; and
- R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl or $C_1$-$C_4$ haloalkoxy.

10. The method of claim 9 wherein
- A is phenyl, naphthalenyl, or a 5- or 6-membered heterocyclic ring, each ring or ring system optionally substituted with halogen;
- R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl or $C_1$-$C_4$ alkoxy;
- M is an alkali metal or $NH_4$; and
- the acid is a weak or moderate acid.

11. The method of claim 10 wherein
- A is phenyl, 2-thienyl, 3-thienyl or 3-pyridyl, each optionally substituted with halogen or $C_1$-$C_4$ alkyl;
- R is methyl or phenyl optionally substituted with $C_1$-$C_4$ alkyl;
- M is Na or K; and
- the acid is acetic acid.

12. A method for preparing a compound of Formula IV

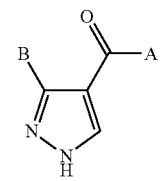

IV wherein
- A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy;
- B is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy;

comprising reacting a compound of Formula I

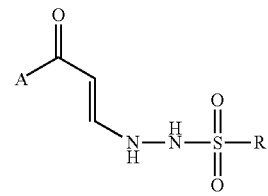

I wherein
- R is $C_1$-$C_8$ alkyl optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy; or
- R is phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, cyano, nitro, phenyl or phenoxy;

with an aldehyde of Formula V

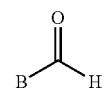

V in the presence of a secondary amine salt.

13. The method of claim 12 wherein

A is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio;

R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl or $C_1$-$C_4$ haloalkoxy; and B is phenyl, naphthalenyl, or a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio.

14. The method of claim 13 wherein

A is phenyl, naphthalenyl, or a 5- or 6-membered heterocyclic ring, each ring or ring system optionally substituted with halogen; and R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl or $C_1$-$C_4$ alkoxy.

15. The method of claim 14 wherein

A is phenyl, 2-thienyl, 3-thienyl or 3-pyridyl, each ring optionally substituted with halogen; and R is methyl or phenyl optionally substituted with $C_1$-$C_4$ alkyl.

16. The compound of claim 1 wherein

A is phenyl substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy.

17. The compound of claim 1 wherein

A is a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy, $C_1$-$C_4$ haloalkylthio, $C_2$-$C_4$ dialkylamino, cyano, nitro, $C_1$-$C_4$ alkoxycarbonyl, phenyl or phenoxy.

18. The compound of claim 17 wherein

A is a 5- or 6-membered heterocyclic ring, each ring or ring system optionally substituted with halogen, $C_1$-$C_4$ alkyl, $C_3$-$C_7$ cycloalkyl, $C_2$-$C_4$ alkenyl, $C_2$-$C_4$ alkynyl, $C_1$-$C_4$ alkoxy, $C_1$-$C_4$ haloalkyl, $C_1$-$C_4$ haloalkoxy or $C_1$-$C_4$ haloalkylthio; and R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl or $C_1$-$C_4$ haloalkoxy.

19. The compound of claim 18 wherein

A is a 5- or 6-membered heterocyclic ring, each ring or ring system optionally substituted with halogen; and R is $C_1$-$C_8$ alkyl optionally substituted with halogen or $C_1$-$C_4$ alkoxy; or phenyl, naphthalenyl or a 5- or 6-membered heterocyclic ring, each ring or ring system optionally substituted with halogen, $C_1$-$C_4$ alkyl or $C_1$-$C_4$ alkoxy.

20. The compound of claim 17 wherein

A is 2-thienyl, 3-thienyl or 3-pyridyl, each optionally substituted with halogen or $C_1$-$C_4$ alkyl; and R is 4-methylbenzene.

\* \* \* \* \*